United States Patent [19]

Seo

[11] Patent Number: 4,509,525

[45] Date of Patent: Apr. 9, 1985

[54] ULTRASONIC DIAGNOSTIC EQUIPMENT

[75] Inventor: Yasutsugu Seo, Ootawara, Japan

[73] Assignee: Tokyo Shibaura Denki Kabushiki Kaisha, Kawasaki, Japan

[21] Appl. No.: 422,174

[22] Filed: Sep. 23, 1982

[30] Foreign Application Priority Data

Dec. 3, 1981 [JP] Japan ............................... 56-193642

[51] Int. Cl.³ ............................................. A61B 10/00
[52] U.S. Cl. ..................................... 128/663; 128/660
[58] Field of Search ............................... 128/663, 660

[56] References Cited

U.S. PATENT DOCUMENTS

| | | | |
|---|---|---|---|
| 3,922,911 | 12/1975 | Groves et al. | 128/663 X |
| 3,940,731 | 2/1976 | Cooper et al. | 128/663 X |
| 4,062,237 | 12/1977 | Fox . | |
| 4,141,347 | 2/1979 | Green et al. | 128/663 |
| 4,152,928 | 5/1979 | Roberts | 128/663 X |
| 4,174,705 | 11/1979 | Buchner . | |
| 4,217,909 | 8/1980 | Papadofrangakis | 128/663 |
| 4,313,444 | 2/1982 | Glenn | 128/663 |
| 4,318,413 | 3/1982 | Iinuma et al. | 128/663 X |
| 4,324,258 | 4/1982 | Huebscher | 128/663 |
| 4,334,543 | 6/1982 | Fehr | 128/663 |
| 4,373,533 | 2/1983 | Iinuma | 128/663 |

FOREIGN PATENT DOCUMENTS 0010304 4/1980 European Pat. Off. .

OTHER PUBLICATIONS

IEEE Trans Sonic & Ultra vol. Su 25 No. 5, 287, 1978.

"Digital Full Range Doppler Velocity Meter" Marco Brandestini.
IEEE Transaction on Sonics and Ultrasonics, vol. SU-17, No. 3, Jul. 1970, pp. 170-185, New York (USA), Donald W. Baker, "Pulsed Ultrasonic Doppler Blood–Flow Sensing".

Primary Examiner—Kyle L. Howell
Assistant Examiner—Francis Jaworski
Attorney, Agent, or Firm—Cushman, Darby & Cushman

[57] ABSTRACT

An ultrasonic diagnostic system is disclosed, which comprises an ultrasonic transducer array having plural transducer elements for transmitting an ultrasonic beam and generating echo signals from the echos reflected from an object, a circuit for exciting the transducer elements to generate the ultrasonic beam that propagates along a predetermined scanning line on the object, and a receiver circuit for time delaying and summing the echo signals to produce a summed output signal. In order to obtain velocity information from a moving object, the equipment further comprises a phase detecting circuit for selecting a Doppler shift signal from the summed output signal to produce a phase detected signal, a digital filter circuit for removing the phase detected signal component reflected from objects moving at lower speed than a predetermined speed from the Doppler shift signal, a circuit for envelope detecting the output signal from the digital filter circuit, a circuit for brightness modulating the amplitude of the output signal from the envelope detecting circuit, and a display unit for displaying the output signal from the brightness modulating circuit as a function of time in real time.

7 Claims, 11 Drawing Figures

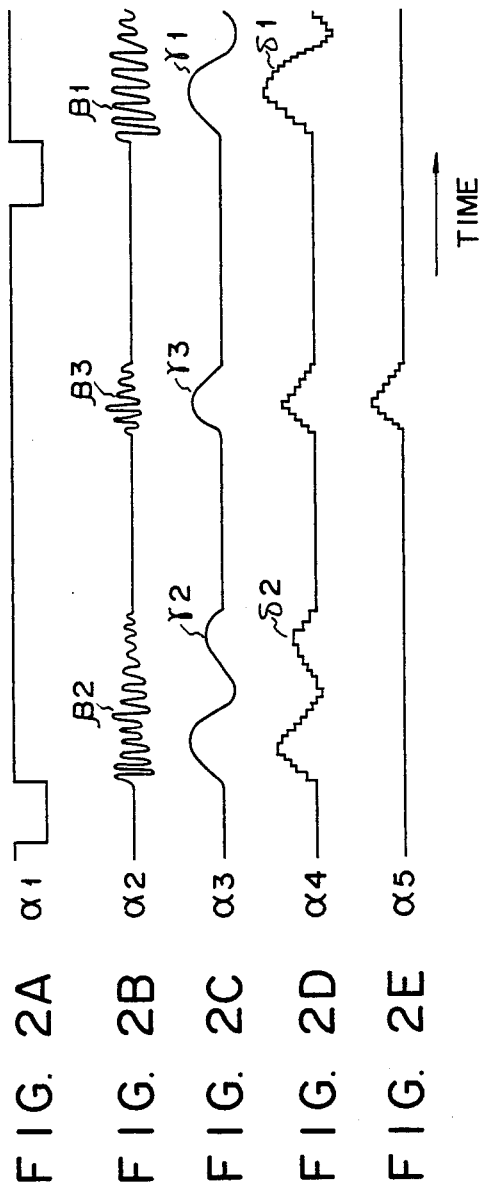
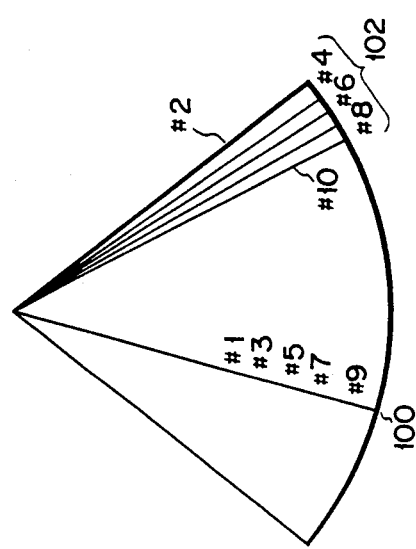
FIG. 2A  FIG. 2B  FIG. 2C  FIG. 2D  FIG. 2E
FIG. 3

ULTRASONIC DIAGNOSTIC EQUIPMENT

BACKGROUND OF THE INVENTION

This invention relates to an ultrasonic diagnostic system for obtaining blood flow velocity information using an ultrasonic Doppler technique.

Recently, it has been known that it is effective to observe the blood flow velocity through the heart simultaneously with obtaining a tomogram, particularly a tomogram of the heart based on ultrasonic pulse echo from the object. As a method of ultrasonically detecting the blood flow state, there is a pulse modulated Doppler technique which has excellent distance resolution.

A system for obtaining blood flow velocity information is disclosed in U.S. Pat. No. 4,217,909 by Emmanuel Papadofrangakis et al. With this system, real time observation of blood flow velocity at a given point in the body can be obtained. However, it is impossible to observe one-dimensional or two-dimensional blood flow velocity distribution.

Marco Brandestini, "Topoflow-A Digital Full Range Doppler Velocity Meter", IEEE Transactions On Sonics And Ultrasonics, Vol. SU-25, No. 5, September 1978, PP. 287-293, discloses a system for obtaining the blood flow velocity distribution in the blood vessel. In this equipment, a Doppler shift signal is separated from a Doppler signal using a digital filter, and the two-dimensional blood flow velocity distribution in a predetermined period of time is obtained by means of frequency analysis of the signal. This equipment requires a circuit for the frequency analysis, therefore, the circuit construction is complicated. Also, the blood flow velocity information cannot be displayed in real time because the blood flow velocity distribution at a fixed time is detected.

SUMMARY OF THE INVENTION

An object of the invention is to provide an ultrasonic diagnostic system, with which one-dimensional blood flow velocity information can be displayed in real time.

The ultrasonic diagnostic system according to the invention includes an ultrasonic transducer array having plural transducer elements, which transmits an ultrasonic beam and generates echo signals from the object. The echo signals contain one-dimensional blood flow velocity information on a predetermined scanning line. This echo signal is received by a predetermined receiving circuit and is phase detected to select a Doppler shift signal from the echo signal. The phase detection signal is supplied to a digital filter circuit to remove the phase detected signal from the object that is moving at a lower speed than a predetermined speed. The output signal from the digital filter circuit is envelope detected, and the amplitude of the signal is brightness modulated. The brightness modulation signal is supplied to a display device for real time display as a function of time. The echo signal contains one-dimensional blood flow velocity information on the scanning line, and the relationships along the depth of the object on the scanning line, time and velocity is displayed on the display device.

With the system according to the invention, the echo signal treated with the digital filter is envelope detected and displayed with time on the display device. Thus, the relationship between all the positions on the scanning line and the velocity information at these positions can be obtained in real time from the display pattern. The equipment according to the invention, unlike the prior art equipment, does not require any frequency analysis. Thus, not only is the construction of the system simple, but also thrombus in the blood vessel can be readily detected since the blood flow velocity information can be obtained in real time.

Further, the effectiveness of the diagnosis can be increased by providing a circuit for obtaining an ultrasonic echo tomogram.

BRIEF DESCRIPTION OF THE DRAWINGS

The above and other objects and advantages will be apparent from the following description taken in conjunction with the accompanying drawings in which:

FIG. 2A is a waveform chart showing a rate pulse $\alpha 1$;

FIG. 2B is a waveform chart showing an output signal $\alpha 2$ from an adder in a receiving circuit;

FIG. 2C is a waveform chart showing a phase detected echo signal $\alpha 3$;

FIG. 2D is a waveform chart showing an A/D converted phase detected signal $\alpha 4$;

FIG. 2E is a waveform chart showing an output signal $\alpha 5$ of a digital filter circuit;

FIG. 3 is a schematic diagram showing the procedure of scanning of a sector scanner according to the invention;

DETAILED DESCRIPTION OF THE PREFERRED EMBODIMENTS

Figure 1:
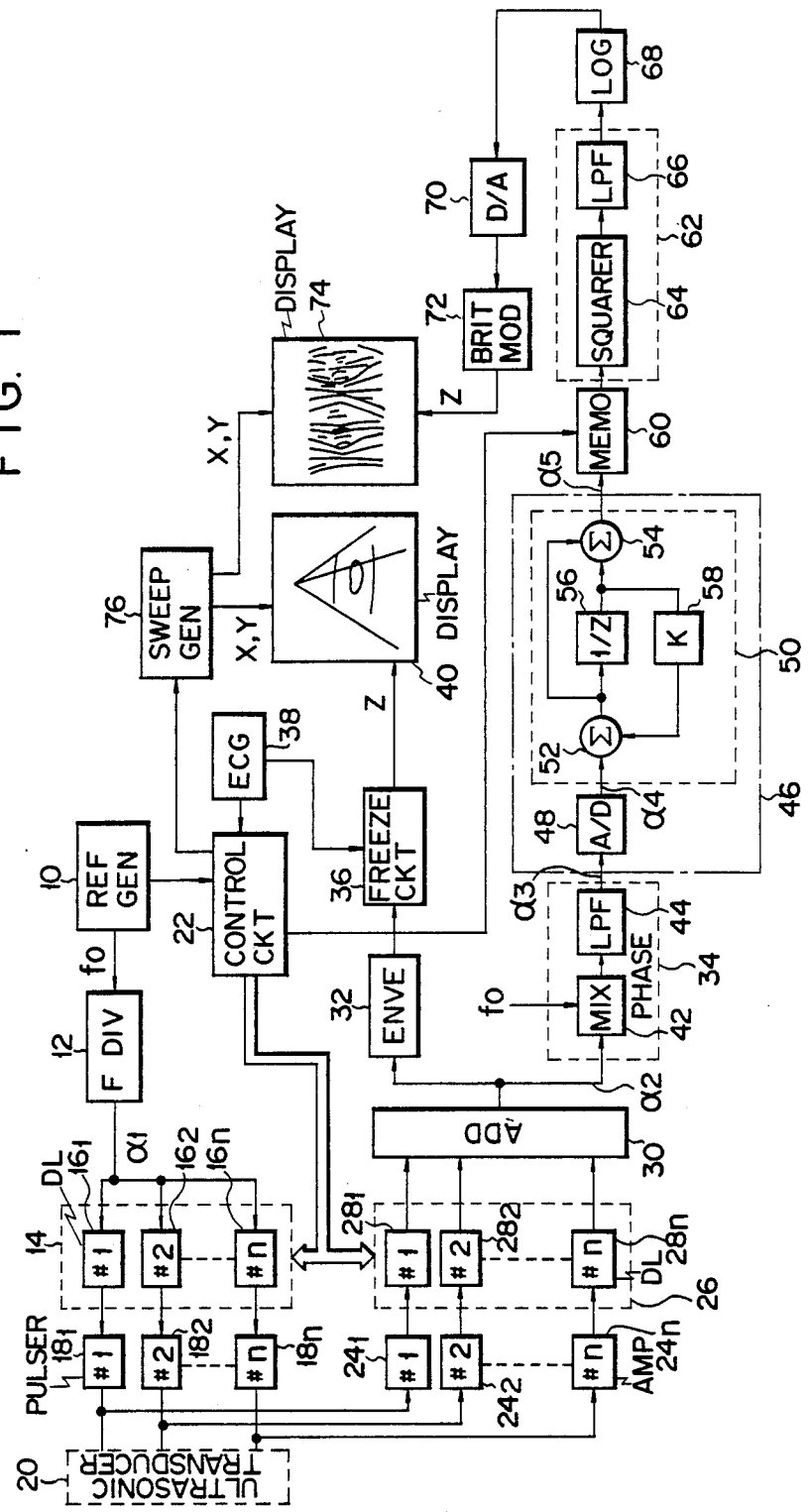
FIG. 1 is a block diagram showing an embodiment of the ultrasonic diagnostic equipment according to the invention.

Now, an embodiment of a sector scanning ultrasonic diagnostic system according to the invention will be described. Referring to FIG. 1, a reference signal generator 10 consists of a crystal oscillator and provides a reference signal $f_o$ having a highly stable frequency characteristic to a frequency divider 12. The frequency divider 12 frequency divides the input signal $f_o$ by N to obtain a rate pulse signal $\alpha 1$ (FIG. 2A). The signal $\alpha 1$ is supplied to a delay circuit 14. When $N=500$ and the reference signal frequency $f_o=2.5$ MHz, the frequency $f_r$ of the rate pulse supplied to the delay circuit 14 is 5 kHz. The delay circuit 14 includes n delay lines $16_1, 16_2, \ldots, 16_n$. The individual delay lines $16_1, 16_2, \ldots, 16_n$ of the delay circuit 14 are connected to respective pulsers $18_1, 18_2, \ldots, 18_n$. The rate pulse signal provided from the frequency divider 12 is thus delayed by predetermined delay times through the delay lines $16_1, 16_2, \ldots, 16_n$ to be supplied to the respective pulsers $18_1, 18_2, \ldots, 18_n$. The pulsers $18_1, 18_2, \ldots, 18_n$ supply delayed pulse signals delayed by predetermined delay times to respective transducers 20, whereby an ultrasonic beam is emitted from each transducer in a predetermined direction. The ultrasonic beam is emitted in synchronism to the rising of the rate pulse. The delay times are controlled by a main control circuit 22.

The ultrasonic beam directed in a predetermined direction reaches an object, for instance a heart, and the echo from a given part of the object is caught by each of the ultrasonic transducers 20. Echo signals thus obtained are supplied to respective amplifiers $24_1$, $24_2$, ..., $24_n$. The outputs of the amplifiers $24_1$, $24_2$, ..., $24_n$ are supplied to respective delay lines $28_1$, $28_2$, ..., $28_n$ of a receiving delay circuit 26 to be delayed there by the same delay times as in the transmitting delay circuit 14. The delay circuit 26 is controlled by the main control circuit 22. One of the delay circuits 14 and 26 may be omitted and the other may be used as a transmitting and receiving delay circuit.

The echo signals delayed by predetermined delay times through the delay circuit 26 are added together by an adder 30. The output of the adder 30 is supplied to a detector 32 for B scan mode operation and also to a phase detector 34 for obtaining blood flow velocity distribution. The echo signal sum output supplied to the detector 32 is envelope detected to obtain tomographic information constituting a B mode ultrasonic echo tomogram. The tomographic information is supplied to a freeze circuit 36. The freeze circuit 36 freezes the input as tomographic information in synchronism to a particular phase of an electrocardiographic waveform produced from an electrocardiographic (ECG) circuit 38. The frozen tomographic information is supplied as a Z signal (which is a brightness signal) to a first display unit 40. The direction in which it is desired to obtain the blood flow velocity in the heart, for instance, is determined while confirming the B scan mode tomographic image of the object.

To obtain blood flow velocity information, the output of the adder 30 is supplied to the phase detector 34. In this case, the main control circuit 22 sets the direction of the ultrasonic beam to a direction in which it is desired to obtain the blood flow velocity information of the object. Alternatively, a scanning line set 100 for obtaining Doppler blood flow velocity information and a scanning line set 102 for obtaining a tomogram may be alternately scanned. That is, #1 may be scanned to obtain Doppler blood flow velocity information, then #2 for obtaining a tomogram, then #3 for obtaining Doppler blood flow velocity information, then #4 for obtaining a tomogram, and so on. By so doing, both the tomogram and Doppler blood flow velocity information can be obtained at the same time.

The phase detector 34 consists of a mixer 42 and a low-pass filter 44. The output signal $\alpha 2$ (FIG. 2B) from the adder 30 is supplied to the mixer 42. The output signal $\alpha 2$ includes signals $\beta 1$ and $\beta 2$ from a fixed or stationary object and a signal $\beta 3$ from a moving object. The reference pulse signal $f_o$ is supplied from the reference signal generator 10 to the mixer 42 to be mixed with the output signal $\alpha a$. In this process, the phase difference between the echo signal from the blood and reference pulse signal $f_o$ is detected so that the Doppler shift of the echo signal can be obtained. The output of the mixer 42 is supplied to a low-pass filter to remove harmonic components. A phase detected signal $\alpha 3$ (FIG. 2C) is thus obtained. The phase detected signal $\alpha 3$ contains a Doppler shift component $\gamma 3$ in various depths in the object interior.

The phase detected signal $\alpha 3$ contains fixed echo signals $\gamma 1$ and $\gamma 2$, for instance from the membrane of the heart. Therefore, the DC component in the signal must be removed. To this end, the output signal $\alpha 3$ from the low-pass filter 44 is supplied to the digital filter circuit 46. The digital filter circuit 46 includes an A/D converter 48 and a filter 50. The output signal $\alpha 3$ of the low-pass filter 44 is converted in the A/D converter 48 into a digital signal $\alpha 4$ (FIG. 2D) which is supplied to the filter 50. The filter 50 includes, for example, adders 52 and 54, a shift register 56 and a multiplier 58. A digital signal component $\delta 1$ supplied through the adder 52 to the shift register 56 is delayed through the shift register 56 by a time corresponding to one rate pulse duration. When the rate pulse frequency $f_r$ is 5 Hz, the rate pulse duration is 200 µsec. The delayed digital signal component $\delta 1$ is fed back through the multiplier 58 to the adder 52 to be added to a digital signal component $\delta 2$ to thereby remove the fixed echo component (FIG. 2E). The output of the adder 52 is supplied to the adder 54 to be added to the aforementioned result, whereby the fixed echo component is further removed. To obtain abrupt filter characteristics, the calculation mentioned above may be repeated in the filter 50 for a period of time corresponding to several 8 rate pulses (200 µsec. × 8 in the case when the rate frequency is 5 kHz).

Figure 4:
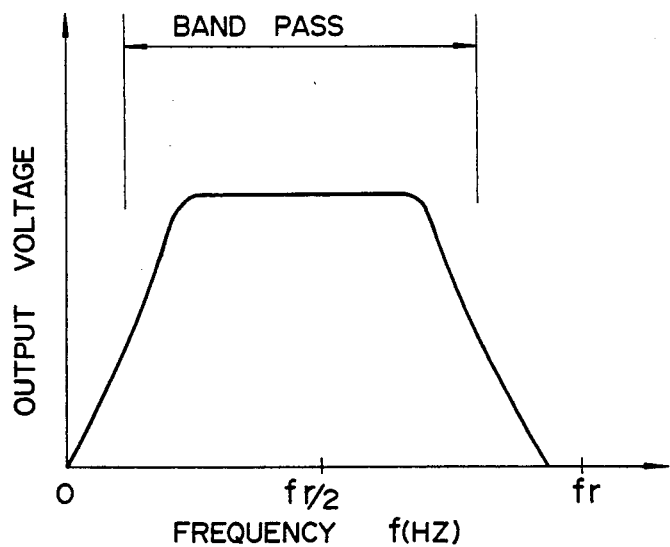
FIG. 4 is a view showing the filter characteristic of a digital filter in FIG. 1.

FIG. 4 shows the filter characteristic of the digital filter circuit 46. The digital filter circuit 46 is a band-pass filter. The circuit 46 has central frequency at one half the rate pulse frequency fr.

The output signal $\alpha 5$ (FIG. 2E) from the filter 50 is temporarily stored in a memory 60. While the filter 50 repeats the calculation for about 8 rate pulses, for instance, the memory 60 holds the output signal $\alpha 5$ and then supplies it to an envelope detector 62. The envelope detector 62 includes a square calculating circuit 64 and a low-pass filter 66. The output signal $\alpha 5$ supplied to the square calculating circuit 64 is squared to obtain a brightness signal, whereby the envelope of the signal is detected. The square signal thus obtained contains harmonic components, so it is supplied to a low-pass filter 66 to remove those components. The output signal of the low-pass filter 66 is supplied to a logarithmic amplifier 68 for logarithmic compression to expand the dynamic range. The logarithmically compressed signal is supplied to a D/A converter 70 for conversion from a digital signal to an analog signal. The analog signal thus obtained, i.e., the Doppler shift signal, is supplied to a brightness modulator 72 for brightness modulation. The output signal of the brightness modulator 72 is supplied as a brightness signal (Z signal) to a second display unit 74. To the second display unit 74 is also supplied an X, Y signal from a sweep signal generator 76 which is controlled by the main control circuit 22. Thus, the blood flow velocity information is displayed as a function of time on real time on the second display unit 74.

Figure 5:
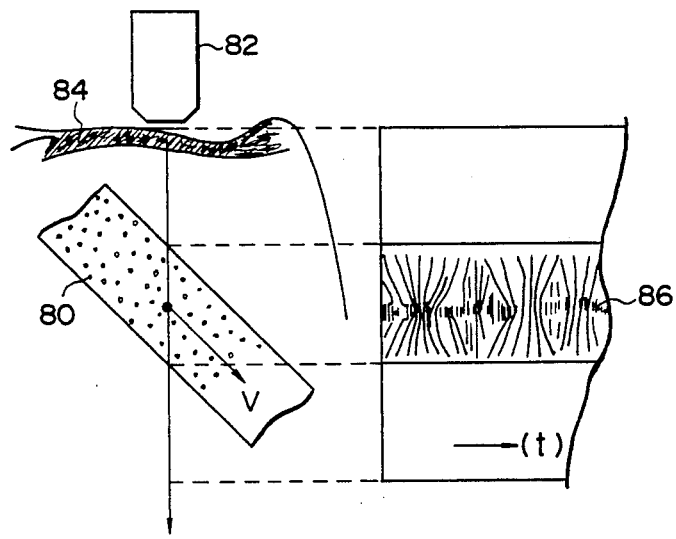
FIGS. 5 and 6 are schematic views illustrating a method of display of a Doppler shift signal with the ultrasonic diagnostic equipment according to the invention.

The operation of the ultrasonic diagnostic equipment according to the invention will now be described in further detail with reference to FIGS. 5 and 6. FIG. 5 shows the result of measurement obtained when there is no thrombus in the blood vessel. An ultrasonic probe 82 is secured to the skin such that it is directed to a blood vessel 80. The ultrasonic echo signal is phase detected and supplied through the filter 50 to the D/A converter 70. It is then brightness modulated and displayed as a pattern 86 on the second display unit 74. In the active blood vessel 80, a small interval stripe pattern is observed for an area of high blood flow velocity, while a large interval stripe pattern is observed for an area where the blood flow velocity is low, as shown in FIG. 5. Thus, the blood flow velocity can be obtained from the interval of the pattern stripes. Where there is no movement or where there is a very slow moving membrane nothing is displayed on the screen due to a filtering effect.

Figure 6:
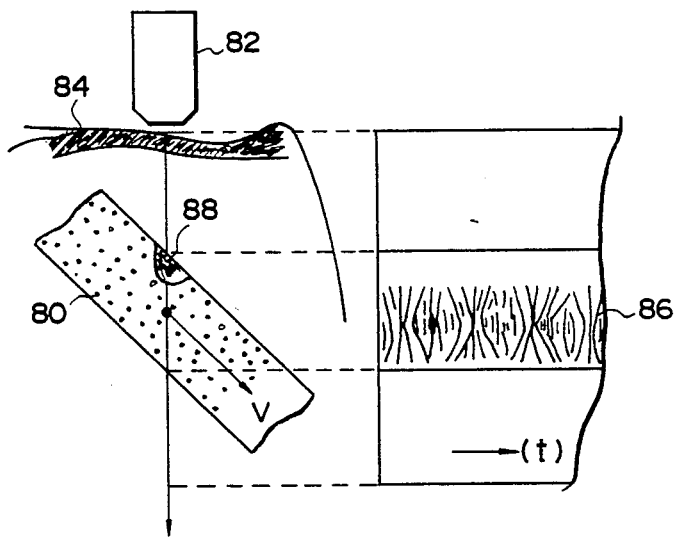

FIG. 6 shows the results of measurement when there is a thrombus 88 in the blood vessel 80. Nothing is displayed for a depth corresponding to the thrombus 88. Thus, the thrombus can be readily detected.

While the above embodiment has used a sector scanner, this invention is applicable to a linear scanner or a mechanical scanner.

Figure 7:
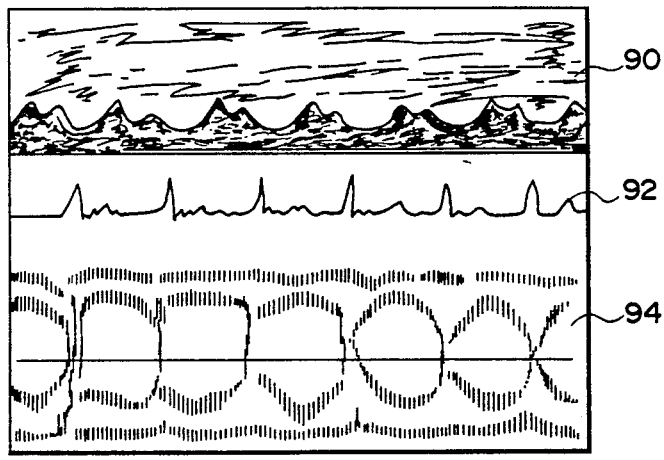
FIG. 7 is a view showing an image displayed on a display device of the ultrasonic diagnostic equipment according to the invention.

The second display unit can display M mode (in which an ultrasonic echo signal representing the movement of the heart valve or the like is displayed together with time), an electrocardiogram (ECG), cardiac sounds and so forth by well-known techniques. FIG. 7 shows a specific image drawn on the second display unit. The pattern 90 shown is that of the M mode representing the instantaneous movement of the heart valve or the like. The pattern 92 is an electrocardiogram. The pattern 94 is obtained by a brightness modulated Doppler shift signal obtained according to the invention.

What is claimed is:

1. An ultrasonic Doppler system for displaying a pattern of a fluid moving within an object, comprising:
    an ultrasonic transducer array having plural transducer elements for transmitting an ultrasonic beam and generating echo signals from the echoes reflected from an object;
    means for exciting said transducer elements to generate the ultrasonic beam that propagates along a predetermined scanning line on the object;
    receiver means for time delaying and summing said echo signals to produce summed output signals representative of echoes along a predetermined scanning line;
    phase detecting means for selecting Doppler shift signals from said summed output signal to produce phase detected signals representative of Doppler shifts associated with points along a predetermined scanning line;
    digital filtering means for removing the phase detected signal component of objects moving at lower speed than a predetermined speed from said Doppler shift signals and for producing digital signals;
    means for squaring the digital signals from said digital filtering means to produce squared signals;
    means for brightness modulating responsive to the amplitude of the squared signals and outputting signal modulated by said amplitudes for representing said fluid pattern at successive depths along said predetermined scanning line to thereby produce an output pattern line; and
    display means for displaying the output signal from said brightness modulating means, said display means comprising means for displaying successive pattern lines as a function of time in real time, whereby said display means displays said fluid pattern without determining the velocity of the fluid.

2. The system according to claim 1, wherein said phase detecting means includes:
    mixer means for mixing said summed output signal and a reference signal; and
    filter means for removing harmonic components in the output signal from said mixer means;
    said digital filter means including:
    means for converting the output signal from said filtering means into a digital signal; and
    filtering means for removing a DC component by taking a difference between said digital signal and an immediately succeeding digital signal for the same part of the object; and
    said squaring means includes:
    means for rectifying the output signal from said digital filtering means by squaring said output signal, and
    filtering means for removing harmonic components in the output signal from said rectifying means.

3. The system according to claim 2, wherein said filtering means is arranged for taking the difference between said digital signal and said immediately succeeding digital signal for the same part of the object repeatedly at least eight times for removing said DC component.

4. An ultrasonic Doppler system for displaying an echo tomogram of an object and blood flow distribution pattern, comprising:
    an ultrasonic transducer array common to both ultrasonic echo and Doppler processes, said ultrasonic transducer array having plural transducer elements and transmitting an ultrasonic beam and generating echo signals from the echoes reflected from said object;
    means for exciting said transducer elements to generate the ultrasonic beam that propagates along first predetermined scanning lines on the object when said ultrasonic echo process is carried out;
    receiver means for time delaying and summing said echo signals to produce first summed output signals representative of echoes along said predetermined scanning lines;
    means for envelope detecting the first summed output signals from said receiver means when said ultrasonic echo process is carried out and for producing envelope detected signals;
    first display means for displaying said envelope detected signals to obtain an echo tomogram of the object;
    means for exciting said transducer elements to generate the ultrasonic beam that propagates along second predetermined scanning lines on the object when said ultrasonic Doppler process is carried out, echos reflected from the object being converted into echo signals, and said echo signals being supplied to said receiver means to produce second summed output signals representative of echoes along said second predetermined scanning lines;
    phase detecting means for selecting Doppler shift signals from said second summed output signals corresponding to said second predetermined scanning lines and for producing phase detected signals representative of Doppler shifts associated with points along said second predetermined scanning lines;
    digital filtering means for removing the phase detected signal component of objects moving at lower speed than a predetermined speed from said Doppler shift signals and for producing digital signals;
    means for squaring the digital signals from said digital filtering means to produce squared signals and outputting a signal representing said fluid pattern;

means for brightness modulating responsive to the amplitudes of the squared signals and outputting signals modulated by said amplitudes for representing said fluid pattern at successive depths along a said second predetermined scan line to thereby produce an output pattern line; and second display means for displaying the output signal from said brightness modulating means, said display means comprising means for displaying successive pattern lines as a function of time in real time, whereby said second display means displays said blood flow distribution pattern without determining the velocity of the blood.

5. The system according to claim 4, wherein said phase detecting means includes:

mixer means for mixing said second summed output signal and a reference signal; and filter means for removing harmonic components in the output signal from said mixer means;

said digital filtering means includes:

means for converting the output signal from said filtering means into a digital signal; and filtering means for removing a DC component by taking the difference between said digital signal and an immediately succeeding digital signal for the same part of the object; and said means for squaring the digital signal including:

means for rectifying the output signal from said digital filtering means by squaring said output signal; and filtering means for removing harmonic components in the output signal from said rectifying means.

6. The system according to claim 5, wherein said filtering means is arranged for taking the difference between said digital signal and said immediately succeeding digital signal for the same part of the object repeatedly at least eight times for removing said DC component.

7. The system according to claim 4, further comprising a freezing means for receiving said envelope detected signal and an electrocardiographic circuit for producing an electrocardiographic waveform, said freezing means receiving said electrocardiographic waveform and transmitting said envelope detected signal in synchronism to a particular phase of said electrocardiographic waveform to said first display means.

* * * * *